United States Patent
Krupnik et al.

(10) Patent No.: US 7,995,798 B2
(45) Date of Patent: Aug. 9, 2011

(54) DEVICE, SYSTEM AND METHOD FOR ESTIMATING THE SIZE OF AN OBJECT IN A BODY LUMEN

(75) Inventors: Hagai Krupnik, Nofit (IL); Amit Pascal, Haifa (IL); Noam Medlinger, Kiryat Tivon (IL); Raphael Rabinovitz, Raanana (IL)

(73) Assignee: Given Imaging Ltd., Yoqneam (IL)

( * ) Notice: Subject to any disclaimer, the term of this patent is extended or adjusted under 35 U.S.C. 154(b) by 967 days.

(21) Appl. No.: 11/907,550

(22) Filed: Oct. 15, 2007

(65) Prior Publication Data

US 2009/0097725 A1    Apr. 16, 2009

(51) Int. Cl.
G06K 9/00 (2006.01)
(52) U.S. Cl. ...................................................... 382/106
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | | | |
|---|---|---|---|---|
| 5,372,502 A | * | 12/1994 | Massen et al. | 433/215 |
| 6,297,488 B1 | * | 10/2001 | Beraldin et al. | 250/201.2 |
| 2001/0051761 A1 | * | 12/2001 | Khadem | 600/117 |
| 2002/0093563 A1 | | 7/2002 | Cline et al. | |
| 2003/0147050 A1 | * | 8/2003 | Nakamura | 353/31 |
| 2004/0092825 A1 | | 5/2004 | Madar et al. | |
| 2004/0127785 A1 | | 7/2004 | Davidson et al. | |
| 2010/0272318 A1 | * | 10/2010 | Cabiri et al. | 382/106 |

FOREIGN PATENT DOCUMENTS

WO    WO 2007/074462    7/2007

OTHER PUBLICATIONS

International Search Report for International Application No. PCT/IL2008/001363 mailed on Feb. 24, 2009.

* cited by examiner

Primary Examiner — Samir Ahmed
Assistant Examiner — Atiba Fitzpatrick
(74) Attorney, Agent, or Firm — Pearl Cohen Zedek Latzer, LLP

(57) ABSTRACT

A device and method for capturing in-vivo images allows for size or distance estimations for objects within the images. According to one embodiment of the present invention there may be provided, in an in-vivo device, at least an imager, an illumination source to provide illumination for the imager, an irradiation source to emit for example a light beam or a laser beam in a body lumen and a processor to calculate, based on image illumination parameter values, an estimate of the size of objects in a body lumen.

16 Claims, 7 Drawing Sheets

DEVICE, SYSTEM AND METHOD FOR ESTIMATING THE SIZE OF AN OBJECT IN A BODY LUMEN

FIELD OF THE INVENTION

The present invention relates to an in-vivo device and method such as for imaging an in-vivo lumen; more specifically, to a method and apparatus in an in-vivo system for estimating the size of an in-vivo object.

BACKGROUND OF THE INVENTION

Known devices may be helpful in providing in-vivo sensing, such as imaging or pH sensing. Autonomous in-vivo sensing devices, such as swallowable or ingestible capsules or other devices may move through a body lumen, sensing as they move along. An autonomous in-vivo sensing device such as an imaging device may include, for example, an imager for obtaining images from inside a body cavity or lumen, such as the gastrointestinal (GI) tract. The imager may, for example, be associated with an optical system, and optionally a transmitter and an antenna. Some of these devices use a wireless connection to transmit image data.

Different methods for estimating the size of objects imaged in a body lumen exist, for example, as described in PCT publication WO2007/074462 to Horn et al., which is directed to a method of determining the size of objects in a body lumen. Horn et al. teach a method of calculating the size of an object in a body lumen, based on for example a laser beam emitted by an irradiation source in the body lumen. The laser beam creates a spot on the image, and if the spot is located on or near the object of interest in the image, the distance to the object and the object's size may be calculated or estimated. However, in situations wherein the spot is not located near the object of interest, the size calculation may not be accurate.

SUMMARY OF THE INVENTION

The present invention introduces a method of determining the size of objects in a body lumen. According to some embodiments, this method may be used to complement known methods in the art.

An embodiment of the device and method of the present invention may enable the estimation or determination of the size of objects seen in in-vivo images from within body lumens or cavities, such as the gastrointestinal (GI) tract.

According to an embodiment of the invention, calculations according to a certain algorithm(s) are performed on the images in order to present to an observer an estimation of the real size (or distance from the imager or from the capsule) of the objects in the image.

According to one embodiment of the invention there may be provided, in an in-vivo imaging device, at least an imager, one or more illumination source(s) to provide illumination for the imager, one or more irradiation source(s) to emit for example collimated light beam(s) or laser beam(s) in a body lumen and a processor to, based on one or more image illumination parameters, calculate, for example, the size of objects in a body lumen or the distance of objects from the in-vivo imaging device.

According to one embodiment of the invention there may be provided a controller to selectively activate the irradiation source(s).

According to one embodiment of the invention there may be provided an in-vivo device comprising an irradiation source to create a light beam spot in the body lumen, an illumination source to illuminate the body lumen, an imager to image the body lumen, and a processor. The processor may receive the image of the body lumen, the image comprising the light beam spot and an object, and may select a first pixel from the image, in correlation to the light beam spot. The processor may further select a second pixel from the image, in correlation to the object. The processor may further calculate image illumination parameter values for the selected pixels and may estimate a distance between the in-vivo imaging device and the object based on the image illumination parameter values.

A method according to one embodiment of the invention may include the steps of emitting light, such as a laser beam optionally from behind an optical dome in an in-vivo imaging device, receiving an in-vivo image from the imaging device (the image including a light beam spot), estimating a distance from the light beam spot to the imaging device, selecting a pixel from the image correlating to the light beam spot, selecting a pixel from the image correlating to an object of interest, calculating values of an image illumination parameter of the pixels; and estimating a distance of the object from the imaging device based on the image illumination parameter values.

A method according to one embodiment of the invention may include calibrating device parameters, and using the calibrated parameter to refine the estimated distance of the object from the imaging device. A method according to one embodiment of the invention may include the steps of calculating the number of pixels that depict the object in the image, and calculating an estimated size of the object.

A method according to one embodiment of the invention may include the steps of creating a model map of the object, for example a three dimensional model map, and presenting the map to a user.

BRIEF DESCRIPTION OF THE DRAWINGS

The present invention will be understood and appreciated more fully from the following detailed description taken in conjunction with the drawings in which.

Figure 1:
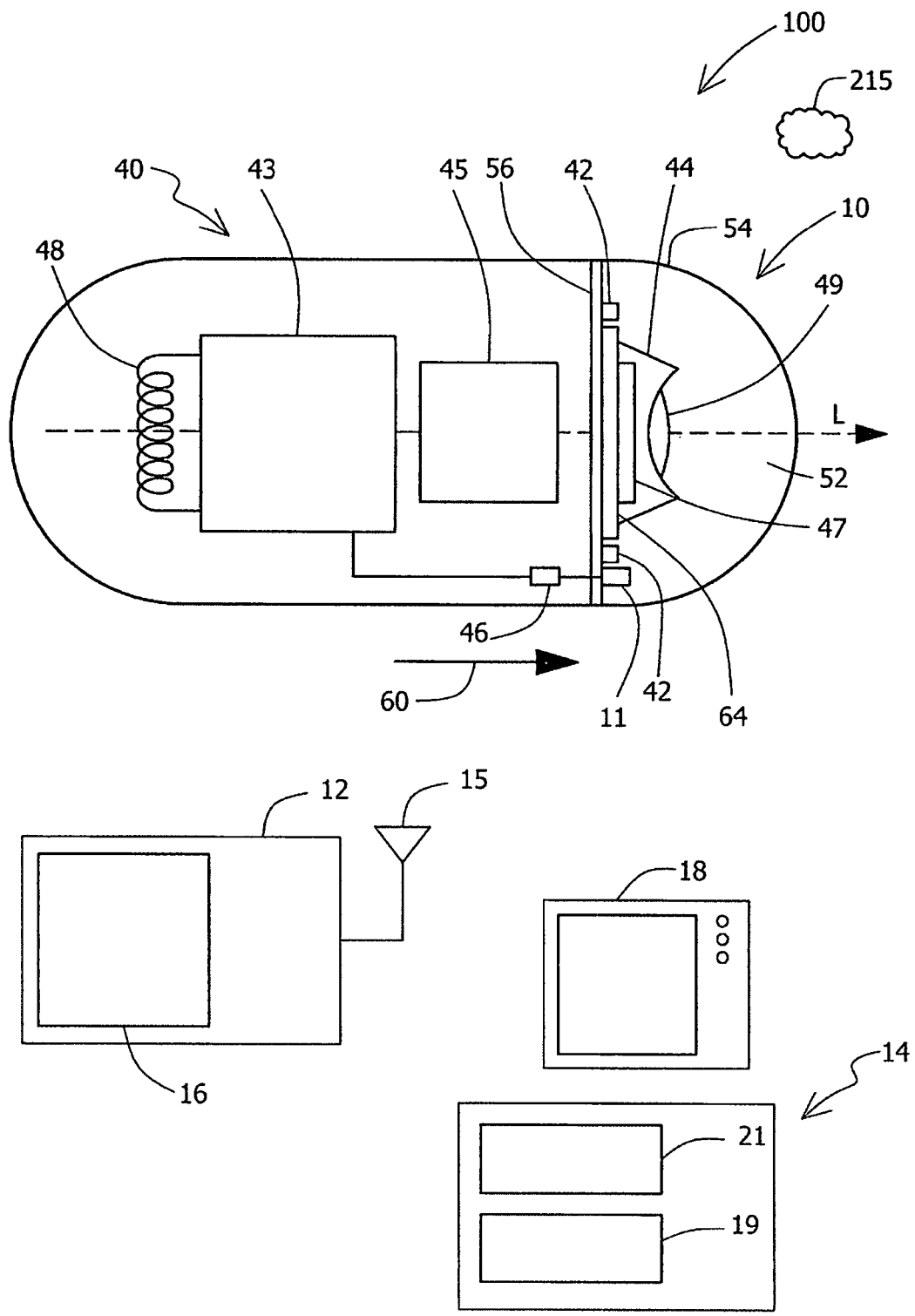
FIG. 1 shows a schematic diagram of an in-vivo imaging system, according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Embodiments of the system and method of the present invention may be used in conjunction with an imaging system or device such as embodiments described in U.S. Pat. No. 7,009,634 to Iddan et al. entitled A DEVICE AND SYSTEM FOR IN VIVO IMAGING, the disclosure of which is incorporated herein. However, the device, system and method according to the present invention may be used with any suitable device, system and method providing imaging and other data from a body lumen or cavity. Various suitable methods of determining the size and distance or estimated distance of an in-vivo object from an in-vivo imaging device may be used, for example methods described in and/or in PCT Publication No. 2007/074462 A2 to Horn et al. entitled SYSTEM DEVICE AND METHOD FOR ESTIMATING THE SIZE OF AN OBJECT IN A BODY LUMEN, the disclosure of which is incorporated herein.

Reference is made to FIG. 1, which shows a schematic diagram of an in-vivo imaging system 100 according to one embodiment of the present invention. The in-vivo imaging system 100 may include, for example an in-vivo imaging device 40. The in-vivo device 40 may be, for example, a swallowable capsule capturing images and possibly other data. The in-vivo device 40 may be in the shape of a capsule, including for example a viewing window or dome 54; other shapes may be used, and the device need not be swallowable or a capsule. Typically, device 40 may include an optical system 10 including, for example, one or more lens(es) 49, lens holder, baffle, or separator 44, a sensor such as an imager 47, for capturing images, and a processing chip or circuit that processes the signals generated by the imager 47. A processing circuit need not be a separate component; for example, processor or a processing chip may be integral to the imager 47. The processing circuit may be divided into several different units or separate components. An illumination source(s) 42, such as a set of light emitting diodes (LEDs), organic LEDs (OLEDs), or other suitable light sources, may provide light to illuminate objects.

Embodiments of the device are typically autonomous and are typically self-contained. For example, the device may be a capsule or other unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

According to one embodiment of the present invention, the device 40 typically may include a transmitter/receiver 43, for transmitting and/or receiving image and other (e.g., non-image) information to a receiving device, and may include other components. The transmitter/receiver 43 may be an ultra low power radio frequency (RF) transmitter with high bandwidth input, possibly provided in chip scale packaging, and may be combined with processing chip or circuit. The transmitter/receiver 43 may transmit and/or receive via for example an antenna 48. The transmitter/receiver 43 may also act as a controller and include circuitry and functionality for controlling the device 40, although a separate control unit may be used. Typically, the device may include a power source 45, such as one or more batteries. For example, the power source 45 may include silver oxide batteries, lithium batteries, or other electrochemical cells having a high energy density, or the like. Other power sources may be used.

Other components and sets of components may be used. For example, the power source may be capable of receiving power from an external power source transmitting power to the device 40, and a controller separate from the transmitter/receiver 43 may be used.

In one embodiment, the imager 47 may be a complementary metal oxide semiconductor (CMOS) imaging camera. The CMOS imager is typically an ultra low power imager and is provided in chip scale packaging (CSP). Other types of CMOS imagers may be used. In another embodiment, another imager may be used, such as a CCD imager, or another imager. According to other embodiments a 320×320 pixel imager may be used. Pixel size may be between 5 to 6 micron. According to some embodiments pixels may be each fitted with a micro lens.

Imager 47 may be fixed or otherwise attached to a substrate such as, for example, circuit board 64 or directly positioned onto a substrate 56. In other embodiments, circuit board 64 may be further attached to a substrate 56, which may for example support illumination source(s) 42 (which may be supported by its/their own substrate or circuit board, which may be supported by or integrated with substrate 56) and which may define a viewing direction 60 of device 40. Substrate 56 may be for example a rigid circuit board or a rigid-flex or completely flexible circuit board. In other embodiments, illumination source(s) may be positioned on a different plane than, for example, imager 47.

Preferably, located outside the patient's body in one or more locations, external to the in-vivo device 40, are a receiver 12, preferably including an antenna or antenna array 15, for receiving image and possibly other data from device 40, a receiver storage unit 16, for storing image and other data, a data processor 14, a data processor storage unit 19, and an image monitor 18, for displaying, inter alia, the images transmitted by the device 40 and recorded by the receiver 12. Typically, the receiver 12 and receiver storage unit 16 are small and portable, and are worn on the patient's body during recording of the images. Preferably, data processor 14, data processor storage unit 19 and monitor 18 are part of a personal computer or workstation, which may include components such as a processor or controller 21, a memory (e.g., storage 19, or other memory), a disk drive, and input-output devices, although alternate configurations are possible. In alternate embodiments, the data reception and storage components may be of another configuration. In addition, a data decompression module for decompressing data may also be included.

According to some embodiments of the present invention, a device such as device 40 may include a distance parameter measurement unit which may include an irradiation output unit or source, such as a dedicated collimated irradiation source 11. In some embodiments the irradiation source 11 may be provided for example, to measure and/or enable determination of the size of an in-vivo object and/or the distance of the in-vivo object from an in-vivo device, such as device 40. The irradiation source may reside externally to the device body, for example, in an extra-body unit. Other components or sets of components may be used.

The irradiation source 11 may be integrated within the in-vivo device 40, typically on at least one side of in-vivo device 40 but optionally in other locations. The irradiation source 11 may periodically or continually emit a light beam or a structured light beam or illuminate, for example a point, a spot, or a grid along a body lumen, which may be imaged, for example by the imager 47. The irradiation source 11 may emit rays, for example monochrome light, laser radiation or white light. The wavelength of the rays emitted by the irradiation source must be within the imager's spectrum sensitivity. The irradiation source 11 may include, for example, laser diodes, regular lenses and/or micro-lenses which may be attached to diodes/detectors, to enable generation and/or reception of point-wise or structured illumination. The irradiation source 11 may include a laser diode such as a Vertical Cavity Surface Emitting Laser (VCSEL). In some embodiments, the irradiation source 11 may include other types of suitable light sources, such as a LED. In some embodiments one or more irradiation source(s) 11 may be provided, positioned on the side(s) and/or other locations, for example integrated on the internal boundary of the shell of in-vivo device 40. In some embodiments a single irradiation source 11 may be provided. In some embodiments, a single beam of light emitted by an irradiation source may be split into several beams, for example by means of a beam splitting unit. A diffractive optic element, a beam shaping unit or other optical element may enable splitting the beam or creating a structured illumination spot or mark.

In a preferred embodiment, the one or more irradiation sources 11 may be positioned on the capsule as far as possible from the center of the imager 47. The irradiation source 11 may be positioned on substrate 56 along with, for example, the illumination source(s) 42. According to some embodiments, the irradiation source 11 may be positioned above the substrate 56, elevated for example above the plane of illumination source(s) 42, and closer to the dome 54, for example by adding a supportive element or a spacing element (not shown).

According to some embodiments, the spot of light created by the irradiation source(s) 11 and reflected from the body lumen may have a higher intensity than the light emitted by illumination source unit (or units) 42. Image data representing the illumination or light beam spot(s) transmitted by the irradiation source may be transferred, by transmitter/receiver 43, to a processor or controller unit, such as, for example, data processor 14. Alternatively, the processor or controller unit may be located within in-vivo device 40, such as, for example, within transmitter/receiver 43 or imager 47. This data may include for example image data of an object 215, the time at which the image was recorded, as well as any other related data, such as intensity, hue, and/or color. The time may be derived from, for example, an in-vivo device 40 master clock, which may be integrated into, for example, an ASIC as part of transmitter 43, reception unit 12, or any other component in in-vivo imaging system 100. In other embodiments, the time need not be transmitted or recorded. The data may be received by reception unit 12, or may be transferred directly to data processor 14. In addition to an image frame there may be a header which may include various telemetry data, such as temperature, pH, pressure, etc.

In some embodiments an activation controller 46 may be provided in the capsule and may be programmable before or after swallowing the capsule. Activation controller 46 may be a separate component, or may be integrated into, for example, an ASIC as part of transmitter 43, reception unit 12, imager 47 or any other component in in-vivo imaging device 40 or in the extra body unit. In some embodiments the irradiation source 11 may be activated, for example, in conjunction with illumination source(s) 42. In some cases, each time one or more illumination sources 42 are activated, the irradiation source 11 is activated simultaneously, and the imager 47 thereby obtains an image of the body lumen area illuminated with both the one or more illumination sources 42 and the irradiation source(s) 11.

In some embodiments, the irradiation source(s) 11 may be activated in an alternating manner, for example switched on in one frame of the imager and switched off in a next frame. The alternating mode may be useful in order to minimize power consumption, and/or to minimize algorithm complexity. For example, the images without the spot may be used for displaying an unobstructed in-vivo image to a user. In some embodiments, the one or more illumination source(s) 42 may be activated in an alternating manner or selectively activated. For example, in one frame only illumination sources 42 may be activated, and in the next frame only irradiation source(s) 11 may be activated. According to some embodiments, two consecutive image frames may be captured by the imager in the in-vivo imaging device, one with the light beam spot(s) and one without it. The time between taking such consecutive images may be very short, for example 0.001 of a second, in order to attempt capturing the same scene in the consecutive frames, and allow minimal time for movement of the in-vivo imaging device during this time. In this manner, each set of two consecutive frames can be used to extract distance and size information of an in-vivo object, without presenting the light beam spot in an image to the user. Other manners of selectively activating and/or alternating the activation of the irradiation source 11 and/or the illumination sources 42 may be used.

Figure 2A:
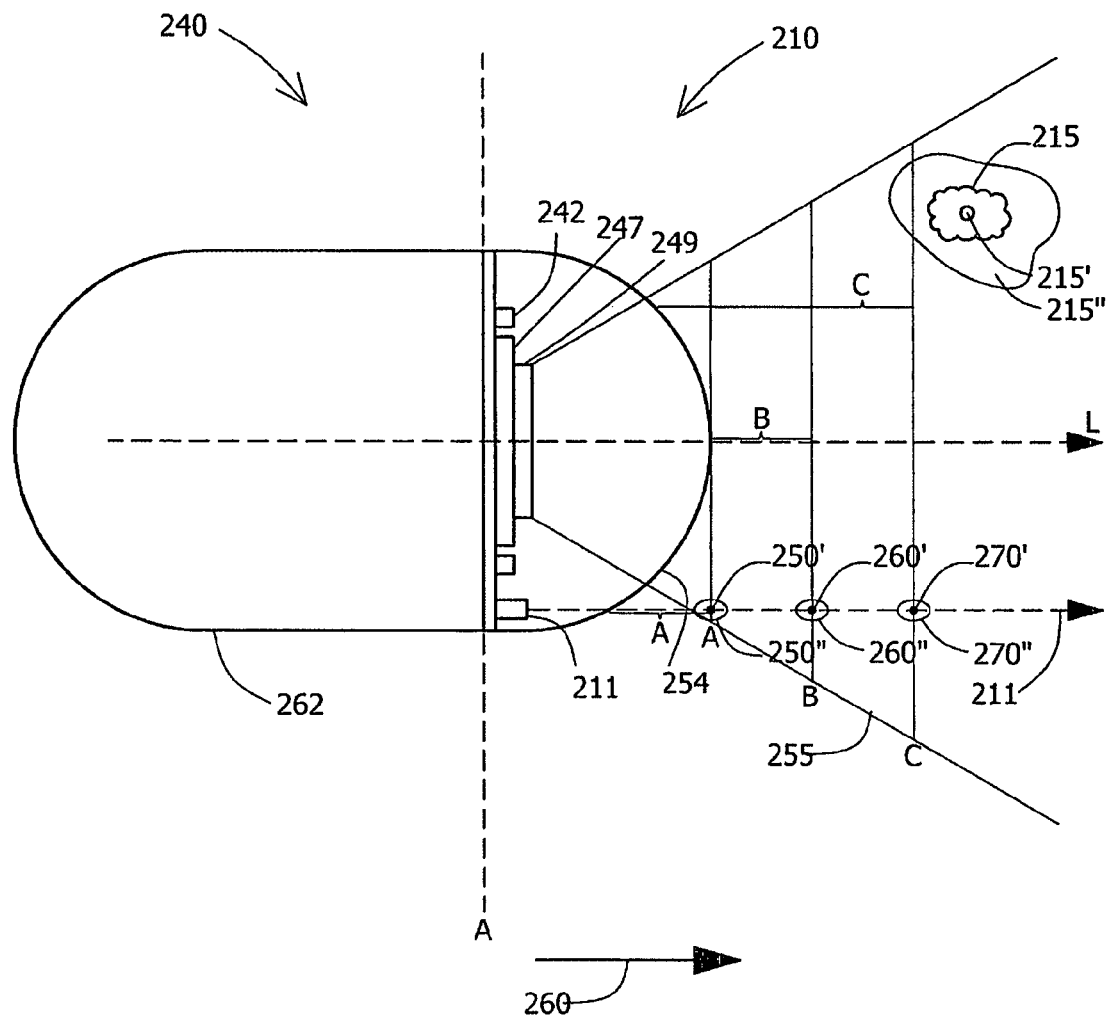
FIG. 2A shows a schematic diagram of an in-vivo imaging device, according to one embodiment of the present invention.

Reference is now made to FIG. 2A, a schematic two dimensional presentation of an in-vivo device 240 according to an embodiment of the present invention. Referring to FIG. 2A, optical system generally referenced as 210 may be included in, for example, device 40 of FIG. 1, but may be included in other suitable devices. Optical system 210 may include, for example, illumination source(s) 242, imager 247, and one or more lenses 249 disposed behind a viewing dome 254, for viewing, for example, a target or object 215. The optical system 210 may include one or more irradiation source(s) 211 such as a collimated light source or laser source for measuring, for example the distance of the object 215 from the in-vivo device 240 (e.g. from the dome 254) and/or the size of the object 215. The one or more illumination source(s) 242 and the one or more irradiation source(s) 211 may be positioned, for example, such that perpendicular axis A intersects both the illumination source(s) 242 and the irradiation source 211.

According to some embodiments of the present invention, the dome 254 may be in one embodiment convex or substantially convex and smooth, and may project outward from the main body and/or housing 262 of device 240 in a "forward" (and/or viewing) direction 260, although note that "forward" is a relative term, as in some embodiments in use the imaging section of device 240 may either lead or follow the rest of the device 240 as it traverses a body lumen. Dome 254 may typically provide for example a Field Of View 255 (FOV) for optical components, such as the imager 247 and the lenses 249 of the in-vivo device 240. For example, the device 240 may, depending on circumstance, traverse a body lumen such that the imager 247 the illumination source(s) 242 and the irradiation source 211 may face the substantially upstream and/or downstream direction, as device 240 may be designed so that there may be two possible directions of travel, both substantially parallel to the axis L of device 240. The direction of travel need not be parallel to the longitudinal axis L, and other configurations (e.g., spherical) may be used. In an embodiment where the device 240 has one or two possible directions of travel (e.g., downstream, or downstream and upstream), the forward end may be defined as being at the end of the device in which the device travels, or one of such ends. In one embodiment, the FOV 255 of the imager 247 via the optical system may be along the longitudinal axis L and towards the "front" end. The device 240 may typically collect images of objects, such as object 215, which may be located generally forward of the forward end of the device 240 (or backward if the device 240 may be facing upstream and progressing downstream), typically up to a 140 degree angle of view although other angles may be used.

Objects, generally beyond the "front" end, such as target or object 215, may be imaged, and the distance of the object 215 from device 240 (e.g. the dome 254) and/or the size of object 215 may be measured by illuminating or emitting for example a collimated light and/or laser beam 211' relative to a direction of travel or imaging of the device 240 e.g. in the direction of the longitudinal axis L.

Figure 2B:
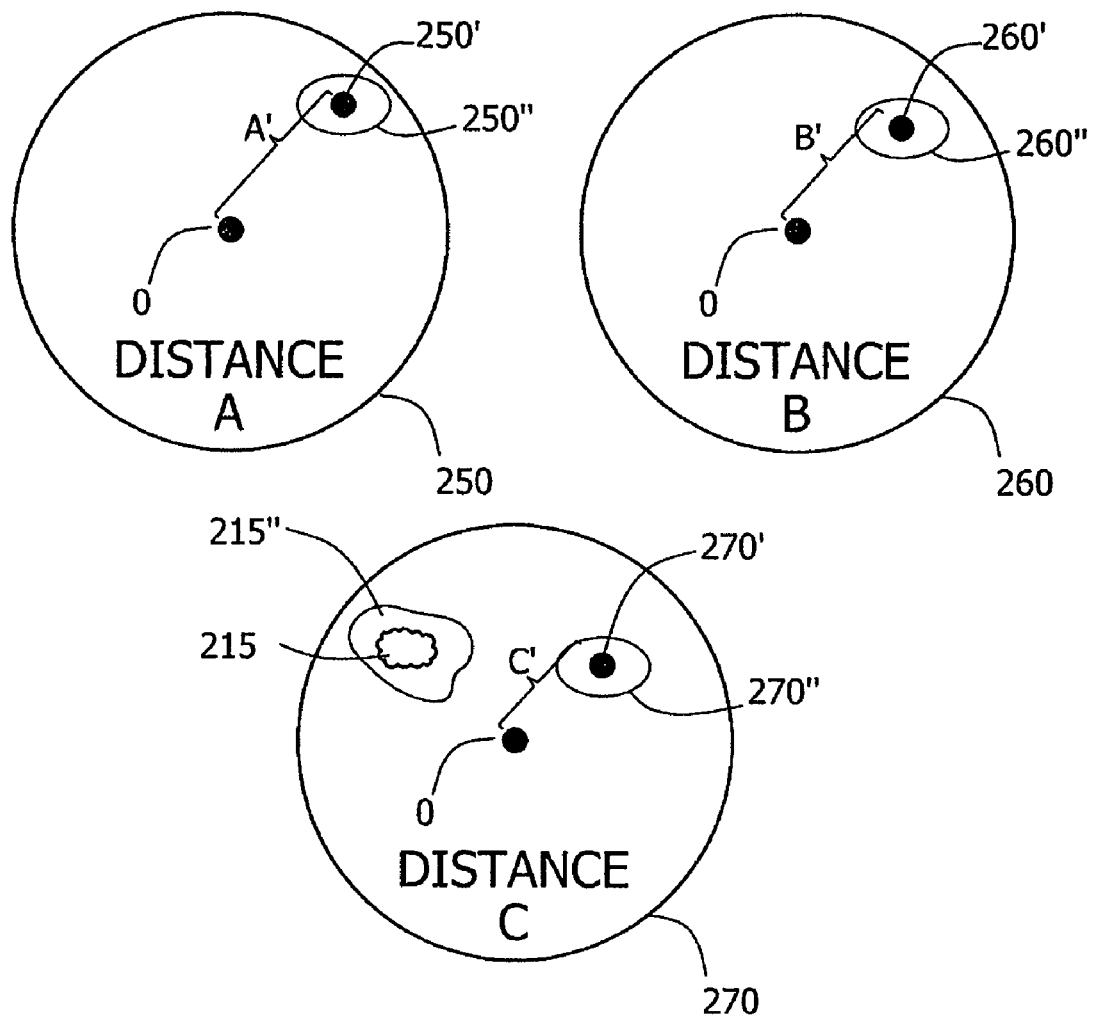
FIG. 2B shows a set of images captured by an in-vivo imaging device, according to an embodiment of the present invention.

Reference is now made to FIG. 2B showing a set of images 250, 260 and 270 which may be captured for example by the in-vivo device 240 of FIG. 2A, according to some embodiments of the present invention. As shown in FIGS. 2A and 2B points 250', 260' and 270' may represent the location of a laser beam 211' in each image 250, 260 and 270. In some embodiments, points 250', 260' and 270' may be detected, and the area surrounding these points marked as 250", 260" and 270" respectively, may be sampled and used for measuring the distance of in-vivo objects such as object 215 from the in-vivo device 240. The location of the laser beam 211' spot in the image (e.g. points 250', 260' and 270'), in images 250, 260 and 270, changes according to the distance of the laser beam spot in the captured image from the in-vivo device 240, e.g. the greater the distance between the laser beam 211' and the in-vivo device, the closer the image of the laser beam (e.g. points 250', 260' and 270') to a point of reference in the image, for example to the center of the image (point O). For example, in image 250, which represents an image captured at a distance A from the device 240 (e.g. 0 mm from the optical dome 254), point 250' is located at a distance A' from the center of image 250 (point O). In image 260, which represents an image captured at distance B from the device 240 (e.g. 10 mm from the optical dome 254), point 260' is located at a distance B' from point O (e.g. A'>B'), while in image 270, which represent an image captured at distance C from the device 240 (e.g. 20 mm from the optical dome 254), point 270' is located at a distance C' from point O (e.g. C'<B'<A'). In some embodiments, depending on the calibration/configuration of the irradiation source(s) and on the selected point of reference in the image, the distance of point 260' from the selected point of reference O may be greater than the distance of point 250' from point O, e.g. A'<B'.

The distance of the laser beam spot from the in-vivo device 240 may be determined/measured by measuring the distance between the laser beam 211' spots (points 250', 260' and 270') in the images 250, 260 and 270 and an arbitrary reference point in the images 250, 260 and 270, such as, for example, point O (the center of the image). For example, the distance between point 270' (e.g. laser beam 211' spot) and point O in image 270 is C'. In a typical embodiment, the position of the irradiation source 11 is known, the distance between the imager and the irradiation source 11 is known, and the angle at which the laser beam is directed is also known. Therefore according to some embodiments, it may be possible to measure the location of the laser spot in the image (e.g., the coordinates of points 250', 260' and/or 270'), and compute the distance of the laser spot from the in-vivo imaging device using simple trigonometric calculations. In an ideal embodiment, the location of the spot in the image may be sufficient to determine the distance of the spot from the in-vivo imaging device. In typical embodiments, it may be required to calibrate specific in-vivo imaging device parameters in each manufactured imaging device, such as the exact position and/or orientation of the irradiation source; and/or the angle at which the laser beam is directed.

In some embodiments, the laser beam spot may be located on the object 215, and it may suffice to calculate the distance to the laser beam spot in order to find the distance to the object 215 or the region of interest. In other embodiments, the laser beam spot may not fall directly on the object 215.

In some embodiments, once the distance between the laser beam spot and the in-vivo imaging device has been determined in a specific image, the distance of the in-vivo object from the in-vivo imaging device in that image, and the actual size of the object, may be estimated. Such estimation may be based on the comparison of the value of the image illumination parameter in an area adjacent to the light beam spot and the value of the image illumination parameter in the vicinity of the target object.

In order to estimate the distance of object 215 from the in-vivo-device 240 (e.g. optical dome 254), particularly where the laser beam spot may not fall directly on the object 215, the pixels in an area correlating to the laser beam spot (250',260',270'), for example an area around the spot (250", 260" and 270") may be sampled. In some embodiments, the sampled area may contain all pixels located up to a selected distance, for example up to 2 pixels, from the center of the spot. In some embodiments, the sampled area may contain the group of pixels located a certain distance, e.g. 4 pixels, from the center of the spot. The sampled area may contain a number of arbitrarily selected pixels in the vicinity of the spot, for example pixels located up to 1 pixel from the boundary of the spot. Other areas may be sampled, for example areas including or excluding a specific color/hue/illumination level.

In some embodiments, an image illumination parameter of the sampled pixels in a selected area correlating to the laser beam spot may be calculated. An image illumination parameter may be calculated for each one of the spots in the image. Such an image illumination parameter may include, but is not limited to, the level of illumination of selected areas in the images, the illumination intensity in selected points or pixels in the image, the grayness level (or luminance) in the sampled area surrounding the laser beam spot and/or the amount of light reflected from the tissue surrounding the laser beam spot. An image illumination parameter may be measured, for example, in units of candela per square meter ($cd/m^2$), lux (cd·sr/m$^2$) or watt per square meter (W/m$^2$). In other embodiments, the level of red, green, blue, infrared, ultraviolet and/or other ranges of wavelengths may be detected/calculated in an area which is in a correlation to the laser beam spot. In some embodiments, an image illumination parameter may be calculated for a single point/pixel or a few points/pixels in the area sampled around the laser beam spot, or in an area correlating to the spot. A larger area may be sampled, for example an area in the diameter of 10 times the diameter of the laser beam spot, surrounding the area of the laser beam spot, and an image illumination parameter may be calculated, for example by averaging the luminance values of all sampled pixels.

The irradiation source(s) or laser(s) may emit light in a specific wavelength range, for example the infrared wavelength range, and an image illumination parameter such as the intensity of the light reflected from the tissue may be detected by using one or more of the imager sensors, for example a red, blue or green imager sensor which may be sensitive to infrared wavelength range. Using a laser in the infrared wavelength range for creating the laser beam spot may be advantageous in reddish environments such as a body lumen, due to sensitivity of the red, blue and green imager sensors in the infrared part of the spectrum. Since the environment is mostly in the red part of the spectrum, it may be advantageous to use the blue imager sensor for receiving the most effective detection of the light beam spot in the image. Other wavelength ranges and/or sensors and/or ratios of detected parameters by different sensors may be used, such as the ratio of the parameter detected by the green imager sensor and the parameter detected by the blue imager sensor.

After calculating the image illumination parameter for the selected pixels in the area correlating to the laser beam spot, a similar process is performed in an area correlating to object 215. The object 215 may be identified manually by a user or may be detected automatically by image analysis software. An area contained in object 215, for example area 215', and/or a selected area surrounding the object, such as area 215" or the area bordered by a set of pixels located a number of millimeters from the boundary of the object 215, may be selected, and the image illumination parameter value per selected pixel in the area may be calculated, and/or an average of the image illumination parameter values. Other parameters of the selected pixels may be used, such as color intensity, hue, saturation, luminance, chromaticity, brightness of the reflected light and/or spectral characteristics and other related data.

According to some embodiments, the brightness, color, hue or saturation of tissue, for example in the GI tract, may be uniform or substantially uniform along the GI tract or sections of the tract. For example, the color of the tissue may be mostly homogeneous. In an ideal system, the illumination of the illumination sources will be distributed uniformly across the field of view of the imager. However, in some embodiments, due to discrete illumination units such as several LEDs, the illumination is not uniform across the imager's field of view. Differences in the brightness, color, hue, chromaticity or saturation of a specific area may be due to differing illumination characteristics (such as distance from the illumination sources or shade) and/or may indicate a pathology or a region of interest on the tissue. For example, the central point in an image may be illuminated more brightly than points located near the edge of the image. The differences in illumination level of pixels in an image which result from the characteristics and structure of the illumination sources may preferably be removed when using the illumination level to calculate the distance or size of an in-vivo object, for example the differences may be removed by creating an illumination map of the image, for example by calibrating each pixel's illumination level.

According to some embodiments, the illumination level of the tissue in an in-vivo image may be relative to the distance of the tissue from the in-vivo imaging device. For example, if the tissue is located relatively far from the in-vivo imaging device, the amount of light reflected back to the imager will be low. Thus, knowing, for example:

1. the distance of a target spot (or point) in an image from an in-vivo device and the illumination level correlating to the spot;
2. the illumination level correlating to an in-vivo object in the image;
3. the number of pixels which the object captures in the image; and
4. the magnification and/or distortion of the optical system in the in-vivo device, it may be possible to measure and calculate, the size of the in-vivo object or the target point, imaged by the in-vivo device, such as device 240. Such a size estimate may be, for example, provided to a user at a processing and/or display system. For many medical purposes, a range of sizes for an object such as provided by the above illustration may suffice. Knowledge of the size of a pathology therefore may enable a physician or other user of a system in accordance with the present invention to decide about urgency of the treatment, type of the treatment, and tools required for the treatment. For example, the size of a detected pathology, such as a polyp, lesion, tumor, cyst, choristoma, hamartoma, tissue malformation or nodule, may correlate to its malignancy.

Figure 2C:
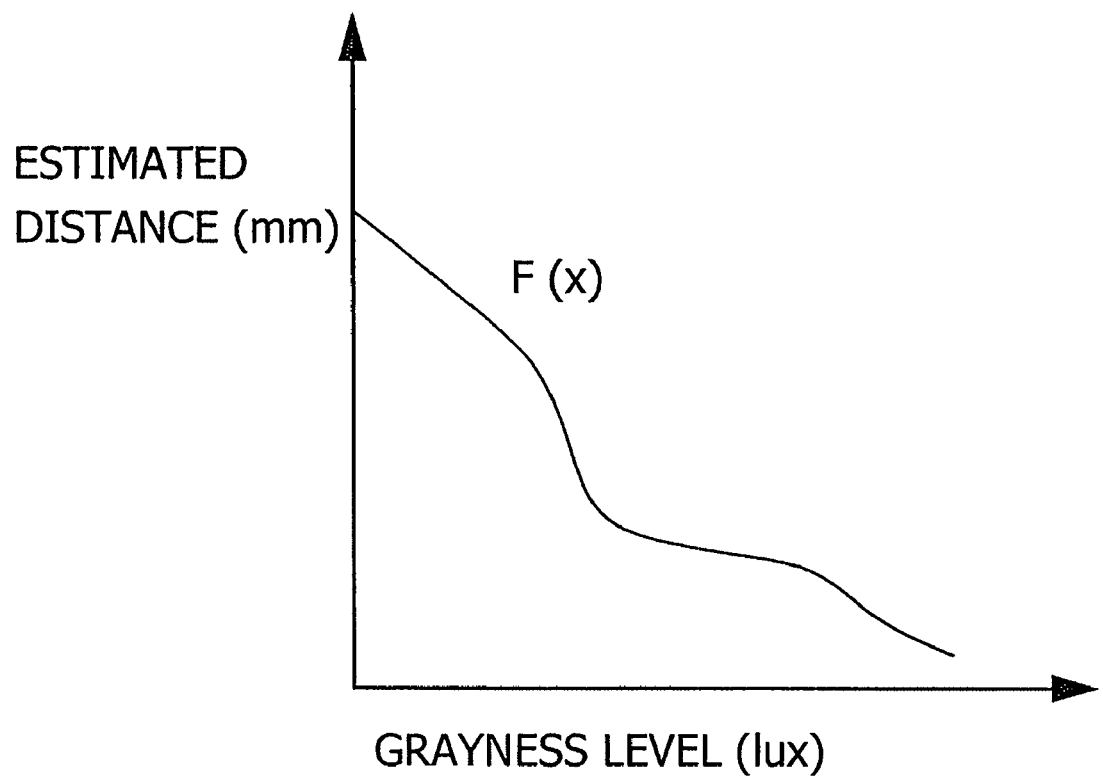
FIG. 2C shows an example of a graph showing an illumination parameter as a function of a pathological object's distance from the in-vivo imaging device.

FIG. 2C depicts an example of a distance graph that may be calculated according to one embodiment of the present invention. According to one embodiment, an illumination or grayness level map describing the initial (or calibrated) image illumination parameter value of each pixel may be measured. The relation between an image illumination parameter value (x) of an area and the distance of that area from the imaging device (F(x)) may be calculated based on the illumination level near a laser beam spot and the calculated distance from the imaging device. One example of such a relation is shown in FIG. 2C. A graph illustrating the relation between a calculated image illumination parameters and the estimated distance of the object from the in-vivo imaging device may be constructed, for example the graph shown in FIG. 2C. Different image illumination parameters may be used in the calculation of the function. For example, the distance function F(x) may be calculated using multiple images with a single irradiation source spot, or preferably, using images with a plurality of irradiation source spots, based, for example, on the method described and shown in FIG. 2B, per a given illumination parameter value (x) of an irradiation source spot. Thus, once the distance function F(x) has been calculated, the distance of any point in an image captured by the device can be inferred from the function. The graph function may change according to different configurations or calibrations of the specific in-vivo imaging device parameters.

Device calibration parameters of the imaging device, for example calibration parameters of the illumination pattern, the illumination strength or intensity, and/or light dispersion pattern of illumination source and/or calibration parameters of the irradiation source may be stored in the in-vivo imaging device and/or transmitted to a reception unit and/or to a workstation. In some embodiments, an estimated location parameter of the irradiation source spot may be a calibrated parameter. An optical system distortion calibration parameter may provide information about the distortion of the image caused by the optical system. Other parameters may be used.

Figure 3A:
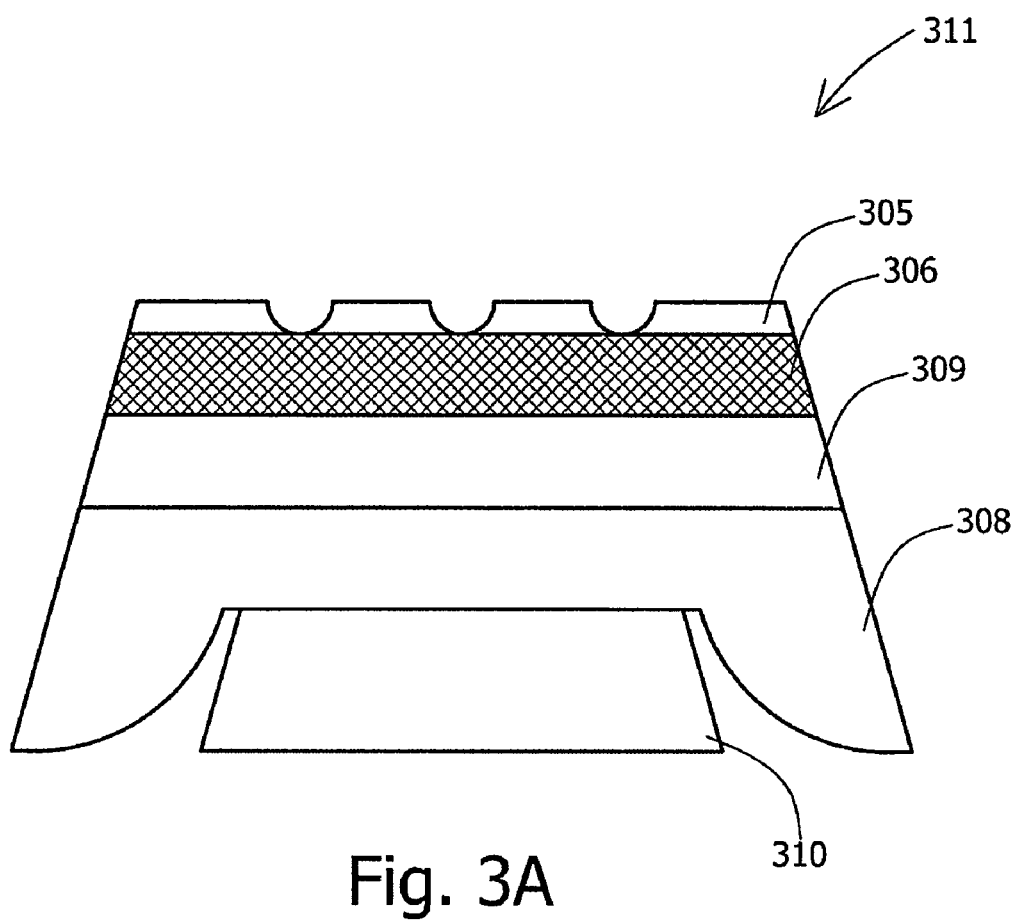
FIG. 3A shows a schematic diagram of a side view of an irradiation source unit, according to an embodiment of the present invention.

Reference is now made to FIG. 3A, which illustrates a side view of an irradiation source unit 311 according to one embodiment of the present invention. The irradiation source unit 311, may include a laser diode 310 such as a Vertical Cavity Surface Emitting Laser (VCSEL) e.g. lasers with a vertical cavity that emit light from their surface in contrast with regular "edge emitters". According to some embodiments the irradiation source unit may include a beam shaping unit e.g. a micro optical element such as a collimating lens 309 and a lens holder 308 for holding, for example the lens 309. According to some embodiments the irradiation source unit may include a beam splitting unit 306 e.g. a micro optical beam splitting component such as a diffractive optic element. The beam splitting unit 306 may split the laser beam into several separate beams, for example three beams that may produce three light spots, which may be used to calculate three different distance measurements in an image. The split beams may be selectively activated by a switch or a controller, for example by using activation controller 46 (shown in FIG. 1). The beam splitting unit 306 may split the irradiation beam into a number of beams. The beam splitting unit 306 may be integrated with the collimating lens 309 and/or with other components of the irradiation source unit 311. In some embodiments, the beam splitting unit 306 may create stray light beams that may interfere with the light beam spot(s) and cause the image analysis or size calculations to be more complex.

According to some embodiments, a blocker element 305 may be included in addition to the beam splitting unit 306. The blocker element 305 may prevent imaging stray light beams that may pass the beam splitting unit 306.

A built in spacing element (not shown) may be included as part of the lens 309 or as a separate component, and may be used to concentrate, focus and/or centralize the beam or beams. A beam shaping unit (not shown) may create a structured light beam spot(s). The irradiation source unit 311 may be made of several separately assembled components, or may be manufactured as a single element.

Figure 3B:
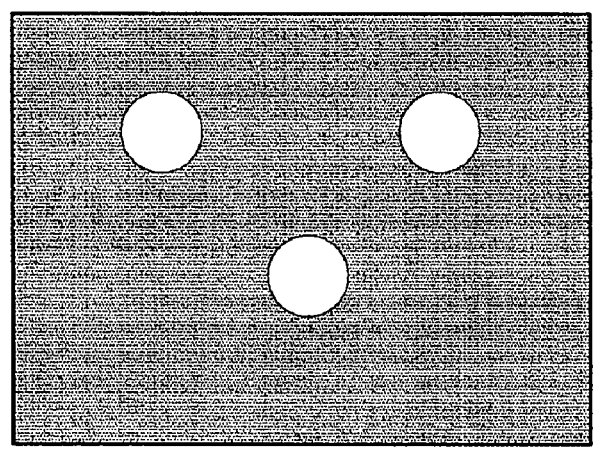
FIG. 3B shows a schematic diagram of a top view of a blocker element, according to an embodiment of the present invention.

FIG. 3B shows an exemplary blocker element as may be viewed from the top, according to one embodiment of the present invention. The blocker element may be made from an opaque material, and may have several transparent openings or apertures that allow light rays, such as a collimated light beam or a laser beam, to pass through. The apertures may be circular, but may have other shapes.

Figure 4:
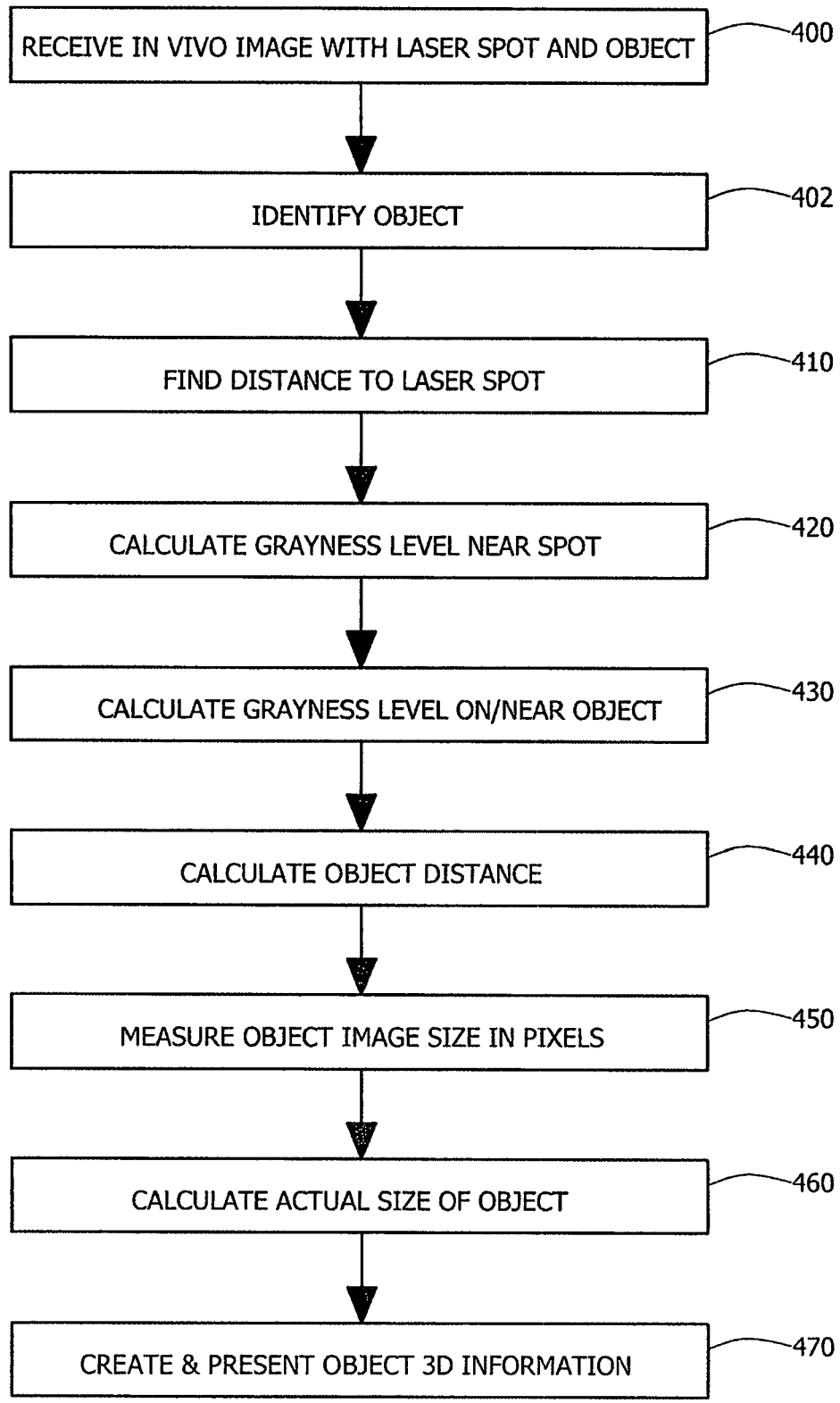
FIG. 4 is a flowchart of a method according to an embodiment of the present invention.

FIG. 4 depicts a series of steps of a method in accordance with an embodiment of the present invention. In step 400, an image including one or more laser beam spots is received from an in-vivo imaging device. In some embodiments, other irradiation sources, for example collimated light or other electromagnetic radiation, may be used to create one or more spots of light in the image. In some embodiments, the spot of light may appear in one image, and the object may appear in another image. The two (or more) images may be used to calculate or estimate the object size, for example by combining both images into a single image using known image registration techniques (for alignment of images of the same or substantially the same scene).

A processor, which may be provided in the imaging device or externally for is example in a receiver or as part of the processing unit in a workstation, receives the in-vivo image data and detects the laser beam spot or spots in it. According to some embodiments, a larger number of laser beam spots (for example 10 spots) may contribute to enhance the accuracy of the calculation/estimation of the in-vivo object size. It may be beneficial to assemble several irradiation sources, and/or to split the beam into several beams in order to create a number of spots in the image. In step 402, a processor may, for example automatically, detect or identify an object of interest, e.g. a pathology, in the image. In some embodiments, a user, for example a physician, may identify the object of interest manually, for example by clicking the mouse on it.

In step 410, a distance from the dome of the in-vivo imaging device to the laser beam spot may be calculated by the processor. The calculation of the distance is performed based on the location of the laser beam spot in the image, for example using the method as depicted in FIG. 2B. In step 420, the grayness level and/or illumination intensity and/or other illumination parameters are calculated for selected pixels in the image, for example in an area in the vicinity or surrounding the laser beam spot. The illumination parameter may be calculated for a single point or pixel near the laser spot image. In step 430, the grayness level, illumination intensity and/or other illumination, color range, hue and/or saturation parameters are calculated for selected pixels in the image, for example in an area in the vicinity or surrounding the object and/or in an area directly on the in-vivo object.

The distance from the in-vivo imaging device to the in-vivo object is then calculated in step 440, for example by comparing the illumination parameter value calculated for a pixel near the laser spot image and the illumination parameter value calculated for a pixel near the object. In step 450, a data processor using computer image analysis techniques, may automatically detect the area of the in-vivo object, or a user may indicate the area of interest for example by dragging the mouse around the in-vivo object presented in the image, or by selecting a central point in boundaries of the object, or by another input method, for example marking the object using a touch screen. In step 460, a size of the in-vivo object or other result may be calculated for example based on the number of pixels which depict the in-vivo object in the image, the calculated distance of the in-vivo object from an in-vivo device, and the magnification and/or distortion of an optical system of the in-vivo device. An estimated size, and/or distance, of for example the in-vivo object, may be displayed to a user for example on a workstation or on a receiver. In another embodiment, the user may only mark the center of the pathology, and computing software may automatically provide an estimated size of an in-vivo object or a selected pathology.

Estimated three dimensional (X, Y, Z) coordinates of selected pixels in the image, e.g. for each pixel that depicts the in-vivo object, or for each pixel contained in the object, may be calculated, by using for example the central point of the optical system of the in-vivo imaging device as the origin point of the axes. In step 470, a model map of the in-vivo object may be created and presented to a user, for example a model map containing three-dimensional information of the in-vivo object. Other models or information may be presented to a user, for example the model map and/or other three-dimensional information relating to the object may enable displaying a virtual or computed image of the object from different angles than the angle that the image was captured by the imaging device. Virtual movement of the imaging device showing the object from different angles may also be displayed. Other steps or series of steps may be used.

In some embodiments, the spot created by a laser or other irradiation source may be visible in the image. The spot may be removed, for example, by image processing techniques such as extrapolation or smoothing the color/texture differences of the tissue behind the spot. Other methods of spot removal may be used. In some embodiments, for example using alternating irradiation source activation, the images with spots may be discarded after extraction of the size analysis data, and only the images without the spots may be presented to a user.

The user of an in-vivo imaging system employing an embodiment of the present invention may, for example estimate the size of an object viewed on the monitor or other image display device. This measurement estimate may be made manually or automatically. For example, by measuring the dimensions of an object viewed on the monitor, and as the magnification and/or the distortion of the optical system of the in-vivo device and the distance of the object from the in-vivo device are known the user may estimate the size of the object.

Alternately, this estimation may be performed automatically. A user may, for example, choose two points on the display (e.g., using a mouse or other user interface with the processing unit), possibly corresponding to the edges of an object, and a data processor unit may provide, for example the size of the object. Other methods of inputting a user indication of an object and outputting a size or size range may be used. Alternately, the data processor or other unit may detect an object of interest, for example a suspected pathology identified using computer image analysis techniques. This may be particularly useful for example where pathologies such as polyps of a certain size range (e.g., 0.5 mm to 1.5 mm) may be diagnosed differently from a polyp of a larger size range (e.g., 1 cm-3 cm). Thus, in this example, using an embodiment of the present invention, even a range of sizes may prove useful for diagnosing one type of polyp or another.

Figure 5A:
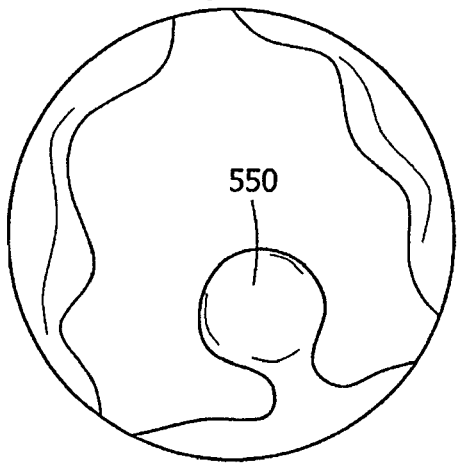
FIG. 5A shows an example of a pathology as presented in an image captured by an in-vivo imaging device.

FIG. 5A shows an example of an object 550 in an image as presented to a user, for example on a monitor display. The in-vivo object of interest may be selected manually by a user, for example by use of a mouse or other input device, and/or may be detected automatically, for example by image analysis processing.

FIGS. 5B-5F show different examples of model maps, for example two-dimensional or three-dimensional model maps, that can be added to a selected object in an image and presented to a user. The models may provide additional information to the user regarding the shape, pattern, form, or structure of the selected object. FIGS. 5B-5F relate to the same object as shown in FIG. 5A.

Figure 5B:
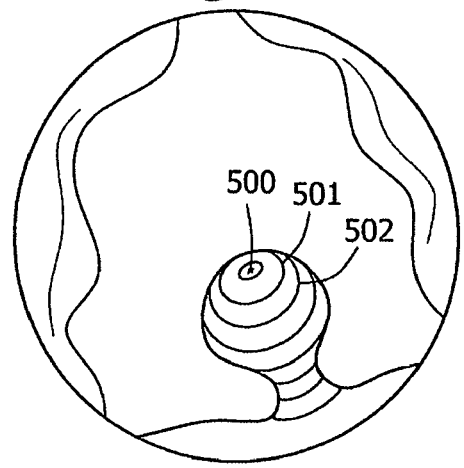
FIG. 5B shows an example of a mapped pathology and displayed to a user.

FIG. 5B shows an example of a model map, which may assist the physician or reviewer in visualization of the in-vivo object and/or the in-vivo object size. The user may mark a single point at or near the center 500 of the object, for example polyp, to be measured. A smoothed version of the image may be computed, for example to smooth out color and/or illumination irregularities. In case the body lumen is not clean, image pixels containing turbid media may be for example ignored. Device calibration parameters of the imaging device may be used to compute a three-dimensional coordinate (X, Y, Z) for each selected pixel around the marked point in the image. A distance map from the point may be constructed, and equal distance contours (501, 502) of for example one (1) millimeter, starting from the marked point 500, may be drawn, creating a 3D representation similar to a topographic map. A length of an aspect of the in-vivo object may be measured along the surface of the 3D representation of the object's model map, thereby obtaining a complete or partial circumference length of the object.

Figure 5C:
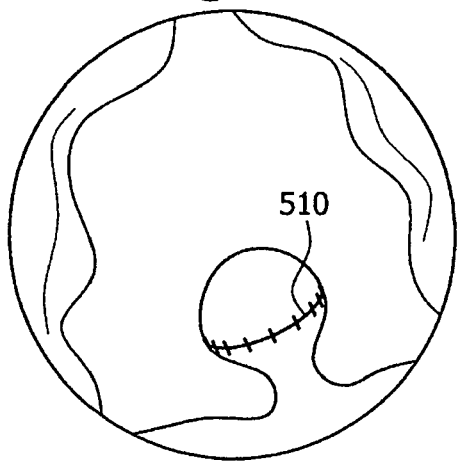
FIG. 5C shows an example of a surface reference ruler added to a pathology and displayed to a user.

FIG. 5C shows another example of a model map, in the form of a surface reference ruler 510 which is added to an image of an in-vivo object. A user may select 2 points on the in-vivo object or other points in the image, for example points 511 and 512, and request a surface reference ruler to be added to the image. Each scale mark on the surface reference ruler depicts for example 1 millimeter. The uneven spaces between the scale marks assist the viewer in understanding the 3D shape and/or the surface shape of the selected object. In some embodiments, a surface reference ruler may be added automatically, for example on a calculated longest visible aspect of a selected and/or detected in-vivo object.

Figure 5D:
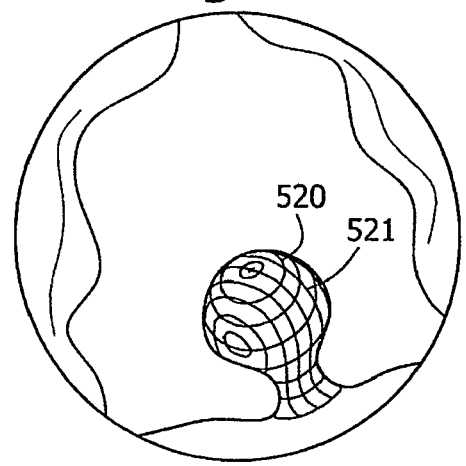
FIG. 5D shows an example of a lattice added to a pathology and displayed to a user.

FIG. 5D shows yet another example of a model map, in the form of a lattice or grid (520, 521) created in a similar method as described previously. The lattice/grid provides additional information to a user for example a health care professional regarding the three dimensional aspects of an object. The distance between each longitudinal line may be for example 1 millimeter, and the distance between each latitudinal line may be for example 1 millimeter. Other distances between lines may be used. The distance between lines in one direction may be different than the distance between lines in the other direction. In some embodiments, a user may draw a line around the pathology, or click on the pathology to mark it. In other embodiments, the pathology may be detected automatically by an image processing algorithm.

Figure 5E:
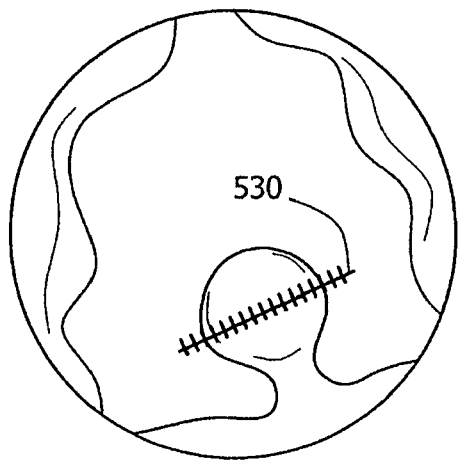
FIG. 5E shows an example of a diameter reference ruler added to a pathology and displayed to a user.

FIG. 5E shows another example of a model map, in the form of a diameter reference ruler 530 added to an image of an in-vivo object. Similarly to the method described in FIG. 6c, a user may select 2 points on the in-vivo object or other points in the image and request a diameter reference ruler 530 to be added to the image. Each scale mark on the diameter reference ruler depicts for example 1 millimeter. The spaces between the scale marks are uniform, and may depict a distance between two selected and/or detected points in the image. For example, the diameter of a selected object may be measured with a diameter reference ruler 530.

Figure 5F:
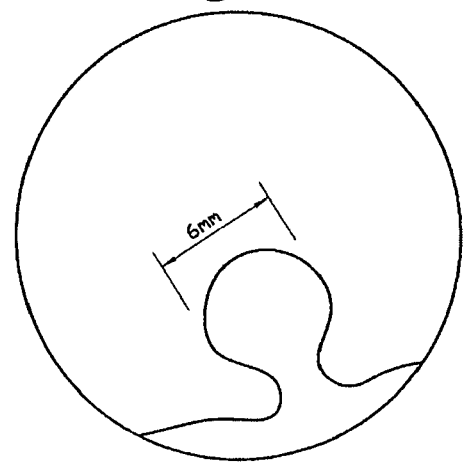
FIG. 5F shows an example of a measurement reference ruler added to a pathology and displayed to a user.

FIG. 5F shows another example of a model map, in the form of a measurement reference ruler added to an image of an in-vivo object. The estimated actual size of the in-vivo object may be presented to a user automatically or upon receiving a request from the user.

While the invention has been described with respect to a limited number of embodiments, it will be appreciated that many variations, modifications and other applications of the invention may be made. Embodiments of the present invention may include apparatuses for performing the calculations and operations herein. Such apparatuses may be specially constructed for the desired purposes or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "estimating", "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove. Rather the scope of the present invention is defined only by the claims, which follow:

What is claimed is:

1. A method of estimating a distance of an in-vivo object from an in-vivo imaging device comprising:
   receiving an in-vivo image from the imaging device, said image comprising a light beam spot and an in-vivo object, wherein the light beam spot does not fall directly on the in-vivo object;
   estimating a distance from the light beam spot to the imaging device; calculating a first illumination property in the vicinity of the light beam spot; calculating a second illumination property in the vicinity of the object; and
   estimating a distance of the object from the imaging device based on the estimated distance of the light beam spot from the imaging device, the first illumination property, and the second illumination property.

2. The method of claim 1 wherein the criteria for calculating the first illumination property is different than the criteria for calculating the second illumination property.

3. The method of claim 1 wherein the illumination properties are selected from a the group consisting of: grayness level, illumination intensity level, luminance, saturation, brightness, color intensity, chromaticity and hue.

4. The method of claim 1 wherein the light beam spot is generated by an irradiation source, wherein said irradiation source is a laser source or a collimated light source.

5. The method of claim 4 wherein the irradiation source is a VCSEL.

6. The method of claim 4 comprising selectively activating the irradiation source.

7. The method of claim 1 further comprising:
   calculating a number of pixels which depict the object in the image; and
   calculating an estimated size of said object.

8. The method of claim 7 further comprising:
   creating a model map of the object; and
   presenting said model map to a user.

9. The method of claim 7 further comprising:
   adding three-dimensional information related to said object to the image; and
   presenting said three-dimensional information to a user.

10. The method of claim 1 further comprising:
    calibrating a device parameter, and
    using said calibrated parameter to refine the estimated distance of the object from the imaging device.

11. The method of claim 10 wherein the device parameter is an optical system distortion parameter, a device illumination parameter, or an estimated location parameter of the irradiation source spot.

12. The method of claim 10 further comprising transmitting the device parameter.

13. The method of claim 1 further comprising removing the light beam spot from the image.

14. The method of claim 1 further comprising identifying the object in the image.

15. The method of claim 1 wherein the object is a pathology.

16. The method of claim 1 wherein the image comprises a plurality of a light beam spots.

* * * * *